US012336494B2

(12) United States Patent
Bérénos et al.

(10) Patent No.: US 12,336,494 B2
(45) Date of Patent: Jun. 24, 2025

(54) **RESISTANCE GENES TO *AGROBACTERIUM TUMEFACIENS* INFECTIONS IN ROSE**

(71) Applicant: Dümmen Group B.V., De Lier (NL)

(72) Inventors: Camillo Bérénos, De Lier (NL); Paulus Cornelis Maris, De Lier (NL); Johannes Wilhelmus Maria van den Biggelaar, De Lier (NL)

(73) Assignee: Dümmen Group B.V., De Lier (NL)

( * ) Notice: Subject to any disclaimer, the term of this patent is extended or adjusted under 35 U.S.C. 154(b) by 270 days.

(21) Appl. No.: 17/786,656

(22) PCT Filed: Dec. 19, 2019

(86) PCT No.: PCT/EP2019/086409
§ 371 (c)(1),
(2) Date: Jun. 17, 2022

(87) PCT Pub. No.: WO2021/121607
PCT Pub. Date: Jun. 24, 2021

(65) Prior Publication Data
US 2023/0025786 A1 Jan. 26, 2023

(51) Int. Cl.
*A01H 6/74* (2018.01)
*C12Q 1/6895* (2018.01)

(52) U.S. Cl.
CPC ........... *A01H 6/749* (2018.05); *C12Q 1/6895* (2013.01); *C12Q 2600/13* (2013.01); *C12Q 2600/156* (2013.01)

(58) Field of Classification Search
None
See application file for complete search history.

(56) References Cited

PUBLICATIONS

GenBank Accession MG970529.1 "Rosa hybrid cultivar clone IIHRR13-4R4 TIR-NBS-LRR resistance protein gene, partial cds" dated Nov. 14, 2018; www.ncbi.nlm.nih.gov/nucleotide/MG970529.1?report=genbank&log$=nuclalign&blast_rank=8&RID=2FGECV1Z013 (Year: 2018).*
Spiller, Monika, et al. "Towards a unified genetic map for diploid roses." Theoretical and Applied Genetics 122 (2011): 489-500. (Year: 2011).*
Li, Shubin, et al. "The development of a high-density genetic map significantly improves the quality of reference genome assemblies for rose." Scientific reports 9.1 (2019): 5985. (Year: 2019).*
Collard, Bertrand CY, et al. "An introduction to markers, quantitative trait loci (QTL) mapping and marker-assisted selection for crop improvement: the basic concepts." Euphytica 142 (2005): 169-196 (Year: 2005).*
Yan, Muqing, et al. "Genotyping-by-sequencing application on diploid rose and a resulting high-density SNP-based consensus map." Horticulture Research 5 (2018). (Year: 2018).*
Muqing Yan et al., "Genotyping-by-sequencing application on diploid rose and a resulting high-density SNP-based consensus map", Horticulture Research, vol. 5, No. 17, (2018). DOI: 10.1038/s41438-018-0021-6.
Shubin Li et al., "The development of a high-density genetic map significantly improves the quality of reference genome assemblies for rose", Scientific Reports, vol. 9, No. 5985, (2019). DOI: 10.1038/s41598-019-42428-y.
Olivier Raymond et al., "The Rosa genome provides new insights into the domestication of modern roses", Nature Genetics, vol. 50, p. 772-777 (2018). DOI: 10.1038/s41588-018-0110-3.

* cited by examiner

*Primary Examiner* — Amjad Abraham
*Assistant Examiner* — Kelsey L Mcwilliams
(74) *Attorney, Agent, or Firm* — The Webb Law Firm

(57) ABSTRACT

Provided herein are rose plants including one or more resistance genes to *Agrobacterium tumefaciens*. Also provided herein are plant parts, cells or reproductive tissue of the plants disclosed herein and methods for identifying *Agrobacterium tumefaciens* resistant rose plants. Specifically, provided herein is an *Agrobacterium tumefaciens* resistant rose plant, wherein the *Agrobacterium tumefaciens* resistance is provided by one or more genes located in linkage group 7 (LG7) of the diploid rose consensus map between 56 to 58.5 Mb and especially one or more genes selected from the group consisting of SEQ ID Nos. 1 to 5.

19 Claims, No Drawings
Specification includes a Sequence Listing.

RESISTANCE GENES TO *AGROBACTERIUM TUMEFACIENS* INFECTIONS IN ROSE

CROSS-REFERENCE TO RELATED APPLICATION

This application is the United States national phase of International Application No. PCT/EP2019/086409 filed Dec. 19, 2019, the disclosure of which is hereby incorporated by reference in its entirety.

The Sequence Listing associated with this application is filed in electronic format via EFS-Web and is hereby incorporated by reference into the specification in its entirety. The name of the text file containing the Sequence Listing is 2203375_ST25.txt. The size of the text file is 40,999 bytes, and the text file was created on Jun. 15, 2022.

BACKGROUND OF THE INVENTION

Field of the Invention

The present invention relates to rose plants comprising one or more resistance genes to *Agrobacterium tumefaciens*. The present invention further relates to plant parts, cells or reproductive tissue of the plants disclosed herein and to methods for identifying *Agrobacterium tumefaciens* resistant rose plants.

Description of Related Art

Crown gall disease is a bacterial disease caused by *Agrobacterium tumefaciens*. Infection by *Agrobacterium tumefaciens* can lead to the formation of galls, as well as stunted growth, chlorotic leaves and increased susceptibility to environmental conditions and secondary infections and can cause large economical losses for rose growers worldwide.

In several other crops, symptom development after inoculation has shown to be heritable, and, based on results obtained using QTL analyses, there is also evidence for dominant monogenic inheritance in several crops such as *Brassica oleracea, Vitis vinifera, Hordeum vulgare* as well a likely recessive inheritance of resistance in *Prunus malaheb*.

In *Arabidopsis thaliana* >100 mutations leading to resistance to transformation by *Agrobacterium tumefaciens* have been described in genes encoding proteins which likely have a role in the plant-bacteria interaction, such as cell wall structure and signal transduction. A role for genes involved in a general defense response has also been found, as a mutation in the transcription factor wrky17 has shown to lead to hyper-sensitivity to transformation by *Agrobacterium tumefaciens* in the same crop.

In rose, however, genetic sources, such as genes or genomic regions, providing resistance, or formulated differently providing absence of crown gall formation after inoculation, to *Agrobacterium tumefaciens* have not been identified. Identifying genes or genomic regions providing resistance against *Agrobacterium tumefaciens* would be of high economic value for rose breeders and rose growers.

Accordingly, there is a need in the art of rose breeding for genomic regions and genes providing *Agrobacterium tumefaciens* resistance to rose plants.

SUMMARY OF THE INVENTION

It is an object of the present invention, amongst other objects, to meet this need in the art of rose breeding.

According to the present invention, the above need in the art is met as outlined in the appended claims.

Specifically, according to the present invention, the above need is met by providing an *Agrobacterium tumefaciens* resistant rose plant, wherein the *Agrobacterium tumefaciens* resistance is provided by one or more genes located in linkage group 7 (LG7) of the diploid rose consensus map between 56 to 58.5 Mb. The diploid rose consensus map has been disclosed by Raymond et al. (2018); "*The Rosa genome provides new insights into the domestication of modern roses*" Nat. Genet. 50:772-778. Further, a rose genome browser is accessible. The present resistance is characterized in the art as an incomplete dominant resistance.

The present one or more genes located in linkage group 7 (LG7) of the diploid rose consensus map between 56 to 58.5 Mb, or the full region between 56 to 58.5 MB, can be derived, or originate, from a rose plant deposited on 23 Sep. 2019 under NCIMB 43507 (NCIMB, Craibstone Estate, Ferguson Building, Aberdeen AB21 9YA, United Kingdom).

According to a preferred embodiment The present one or more genes located in linkage group 7 (LG7) of the diploid rose consensus map between 56 to 58.5 Mb, or the full region between 56 to 58.5 MB, are identical to the corresponding genes or region of a rose plant deposited under NCIMB 43507.

According to a preferred embodiment of the present invention, one of the one or more genes located in linkage group 7 (LG7) of the diploid rose consensus map between 56 to 58.5 Mb is a gene encoding the cDNA sequence of SEQ ID No. 6. SEQ ID No. 6 is designated in the diploid rose consensus map as RchiOBHmChr7g0232931 (position: end=57131496 begin=57128076).

In *Agrobacterium tumefaciens* resistant rose plants, as compared to *Agrobacterium tumefaciens* susceptible plants, the nucleotide at position RoseV2_RchiOBHmChr7_57128943 is mutated from T to A. The upstream and downstream nucleotides around position RoseV2_RchiOBHmChr7_57128943 (in *Agrobacterium tumefaciens* resistant rose plants) are represented by SEQ ID No. 11.

According to another preferred embodiment of the present invention, one of the one or more genes located in linkage group 7 (LG7) of the diploid rose consensus map between 56 to 58.5 Mb is a gene encoding the cDNA sequence of SEQ ID No. 7. SEQ ID No. 7 is designated in the diploid rose consensus map as RchiOBHmChr7g0232831 (position: begin=57010720 end=57017672).

In *Agrobacterium tumefaciens* resistant rose plants, as compared to *Agrobacterium tumefaciens* susceptible plants, the nucleotide at position RoseV2_RchiOBHmChr7_57010803 is mutated from C to G. The upstream and downstream nucleotides around position RoseV2_RchiOBHmChr7_57010803 (in *Agrobacterium tumefaciens* resistant rose plants) are represented by SEQ ID No. 12.

According to yet another preferred embodiment of the present invention, one of the one or more genes located in linkage group 7 (LG7) of the diploid rose consensus map between 56 to 58.5 Mb is a gene encoding the cDNA sequence of SEQ ID No. 8. SEQ ID No. 8 is designated in the diploid rose consensus map as RchiOBHmChr7g0232901 (position: begin=57087871 end=57092473).

Absence of the coding sequence (SEQ ID No. 8) is associated with susceptibility to *Agrobacterium tumefaciens* and presence of the coding sequence (SEQ ID No. 8) is associated with resistance to *Agrobacterium tumefaciens*.

According to yet another preferred embodiment of the present invention, one of the one or more genes located in linkage group 7 (LG7) of the diploid rose consensus map between 56 to 58.5 Mb is a gene encoding the cDNA sequence of SEQ ID No. 9. SEQ ID No. 9 is designated in the diploid rose consensus map as RchiOBHmChr7g0232961 (position: begin=57174178 end=57174936).

In *Agrobacterium tumefaciens* resistant rose plants, as compared to *Agrobacterium tumefaciens* susceptible plants, the nucleotide at position RoseV2_RchiOBHmChr7_57175177 positioned 241 nucleotides upstream of the start codon is A. The upstream and downstream nucleotides around position RoseV2_RchiOBHmChr7_57175177 (in *Agrobacterium tumefaciens* resistant rose plants) are represented by SEQ ID No. 13.

According to still another preferred embodiment of the present invention, one of the one or more genes located in linkage group 7 (LG7) of the diploid rose consensus map between 56 to 58.5 Mb is a gene encoding the cDNA sequence of SEQ ID No. 10. SEQ ID No. 10 is designated in the diploid rose consensus map as RchiOBHmChr7g0232471 (position: begin=56575965 end=56579420).

In *Agrobacterium tumefaciens* resistant rose plants, as compared to *Agrobacterium tumefaciens* susceptible plants, the nucleotide at position RoseV2_RchiOBHmChr7_56578406 is mutated from C to G. The upstream and downstream nucleotides around position RoseV2_RchiOBHmChr7_56578406 (in *Agrobacterium tumefaciens* resistant rose plants) are represented by SEQ ID No. 14.

Considering the above, the present invention relates to the following most preferred embodiments:
- an *Agrobacterium tumefaciens* resistant rose plant wherein the one or more genes located in linkage group 7 (LG7) of the diploid rose consensus map between 56 to 58.5 Mb is a gene encoding the cDNA sequence of SEQ ID No. 1.
- an *Agrobacterium tumefaciens* resistant rose plant wherein the one or more genes located in linkage group 7 (LG7) of the diploid rose consensus map between 56 to 58.5 Mb is a gene encoding the cDNA sequence of SEQ ID No. 2.
- an *Agrobacterium tumefaciens* resistant rose plant wherein the one or more genes located in linkage group 7 (LG7) of the diploid rose consensus map between 56 to 58.5 Mb is a gene encoding the cDNA sequence of SEQ ID No. 3.
- an *Agrobacterium tumefaciens* resistant rose plant wherein the one or more genes located in linkage group 7 (LG7) of the diploid rose consensus map between 56 to 58.5 Mb is a gene encoding the cDNA sequence of SEQ ID No. 4.
- an *Agrobacterium tumefaciens* resistant rose plant wherein the one or more genes located in linkage group 7 (LG7) of the diploid rose consensus map between 56 to 58.5 Mb is a gene encoding the cDNA sequence of SEQ ID No. 5.

According to an especially preferred embodiment, the present rose plants are hybrid rose plants.

According to yet another especially preferred embodiment, the present *Agrobacterium tumefaciens* resistant rose plants comprising at least two copies of the present one or more genes providing *Agrobacterium tumefaciens* resistance.

According to still another especially preferred embodiment, the present invention relates to *Agrobacterium tumefaciens* resistant rose plants comprising a tetraploid genome and at least 3 copies, preferably 4, of the present one or more genes providing *Agrobacterium tumefaciens* resistance.

According to yet another especially preferred embodiment, the present *Agrobacterium tumefaciens* resistant rose plants comprise combinations of the above defined resistance providing genes such as a combination of SEQ ID No. 1 and SEQ ID No. 2 or SEQ ID No. 11 and SEQ ID No. 12; SEQ ID No. 1, SEQ ID No. 2 and SEQ ID No. 3 or SEQ ID No. 11, SEQ ID No. 12 and SEQ ID No. 13; SEQ ID Nos. 1 to 4; SEQ ID Nos. 1 to 5 or SEQ ID Nos. 11 to 14.

The present invention also relates to plant parts, cells or reproductive tissue of the present *Agrobacterium tumefaciens* resistant rose plants.

The present invention further relates to methods for identifying an *Agrobacterium tumefaciens* resistant rose plant, the method comprises the step of establishing the presence of one or more genes or allelic copies thereof encoding a cDNA sequence selected from the group consisting of SEQ ID Nos. 1 to 5 in the genome of said rose plant or establishing the presence of one or more sequences selected from the group consisting of SEQ ID Nos. 11 to 14 in the genome of said rose plant.

DESCRIPTION OF THE INVENTION

The present invention will be further detailed in the example presented below.

Example

Material & Methods
Population Development and Phenotypic Screen

A tetraploid F1 *Rosa hybrida* population was created by hand-pollinating a tetraploid cut rose with a rose accession. This cross resulted in 353 F1s, which were tested for *Agrobacterium tumefaciens* resistance. The parents were also tested. The *A. tumefaciens* isolate that was used originated from the Netherlands and was isolated in 1992. It was multiplied on artificial medium and used at a final inoculum density of $2.6 \times 10^9$ colony forming units/ml. For each accession (F1 individuals and parents) 5 rooted cuttings were transplanted in 14 cm pots, one week upon inoculation. Inoculated plants were put in randomized block design, 4 plants for each accession. One plant per accession was inoculated with water. Plants were inoculated by making an incision in the stem with a scalpel that was dipped in the inoculum. After each incision, scalpel was dipped again. The bio-assay was carried out under long-day conditions with a temperature set at 22° C. and 20° C. for day and night respectively. Relative humidity was set at 70%. For each plant, tumor presence was scored and size was measured 3, 5, 7, 9, 11, and 14 weeks after inoculation.

Phenotypic Data Analysis

A total of 8572 observations for 1412 plants of 353 unique F1 genotypes were scored for tumor size and presence. Response variables were analysed using a mixed-model framework using the sommer package (Covarrubias-Pazaran 2016) in R. Both genotype and block were fitted as random effects, and for tumor size week of observation was included as a fixed effect (covariate). Broad sense heritability was then calculated by dividing the genotypic variance by the sum of the variance components. Best Linear Unbiased Predictors (BLUP) were obtained for each genotype and used as corrected phenotypes for downstream analyses.

Corrected phenotypes are centered around 0 (which defines the population mean) and deviations are expressed in the measurement units.

Genetic Analyses

Genotyping: A panel consisting of F1 plants, parents and broad germplasm accessions were genotyped using the WagRhSNP Axiom SNP array. This chip contains 68'893 SNPs which are targeted by two probes from each direction. Initial quality control and dosage calling was performed using the R package FitPoly (non-default settings:p.threshold=0.95, call.threshold=0.65, peak.threshold=0.975). Further QC was performed using custom-made scripts in R. Non-segregating SNPs, SNPs where the most common genotype had a frequency of >81% and SNP markers with more than 10% missing data were removed resulting in a dataset containing 46'539 markers. A total of 298 F1 individuals were successfully genotyped.

SNPs were mapped to the Rose Genome assembly (Raymond et al. 2018) by blasting flanking sequences against the reference using local blast (settings: -evalue 1-outfmt 6-max_target_seqs 1-max_hsps 1). Using custom scripts in R only blast hits were retained with alignment length greater than 50 and percentage of identical matches greater than 85.

Association analyses:Marker-trait analyses were performed using a mixed-model GWAS framework using the sommer package (Covarrubias-Pazaran 2016) in R where SNPs were fitted as fixed effects and a genomic relationship matrix (GRM) was fitted as a random effect to account for population structure and residual polygenic effects (genetic effects not caused by the SNP of interest). Genomic heritability was also calculated similarly, by analyses the corrected phenotypes by fitting a GRM as a random effect.

Annotation analyses:Gene predictions in QTL regions were extracted from two files. The first was the Eugene Annotation v1.1 without repeats (RchiOBHm-V2-EGN-r1.1.without_TE.gff). The second were the gene predictions obtained using blast2Go (RchiOBHm-V2-EGN-r1.blast2go.20170310.MAPPING) (Raymond et al. 2018).

A gene was considered a resistance gene if the gene predictions contains at least one of the following terms:

kinase, phosphatase, (PP2C), VIP1, Caspase, GALLS, interacting, CAK2Ms, Caspase, Histones, Histone, pCsn5-1, DNA, ligase, IVa, Nucleosome, assembly, CAF-1, Histone, H3, chaperoneGA1, Histone, deacetylases, H4, H3-11, H2A, Myb, transcription, factor, wrky, wrky17 (Gelvin 2010; Lacroix and Citovsky 2013).

A total of 60 broad germplasm accessions (including the resistant source) were whole-genome-sequenced. Reads were QC-ed and SNPs were called after mapping the reads to the *Rosa chinensis* reference genome (Raymond et al. 2018).

Validation Using SNPs

We mined for high-utility SNPs by 1) selecting resistance genes in the QTL region; 2) identifying SNPs in those genes that showed alleles that were uniquely or almost uniquely found in the source; 3) only retaining SNPs for which KASP assays could be designed.

KASP assays were designed and first tested on a small panel of accessions to determine if they amplified. KASP assays that amplified were then run on two F1 populations sharing the same resistant parent to identify the SNPs that were most highly associated with *A. tumefaciens* resistance. After finemapping, the SNPs were used to screen a panel of broad germplasm to determine the occurrence of resistance alleles in the germplasm.

Results

Tumor incidence (the percentage of plants with visible tumors) increased from 22.5% 3WAI (Weeks After Inoculation) to 65.7% 14WAI. Of the 484 plants that were tumor-free 14 WAI, 35 genotypes were symptomless for all 4 reps (a total of 140 plants), and a further 54 genotypes were symptom-free for 3 replicates. The remaining symptom-less plants belonged to genotypes that displayed more heterogeneity in tumor score. Mean gall size increased from 5.69 3WAI to 14.66 mm 14 WAI (Table 1), with a maximum gall size of 62.65 mm Mean gall sizes (in mm) at 14WAI for the references (e.g. resistant/susceptible and used for normalization between experiments) were as follows: RS-1075: 48.8, RS-1183: 38.6, RS-1408: 36.28, RS-1418: 0, RS-9052: 15.9.

TABLE 1

Progression of tumor incidence during the 14 week long experiment.

| WAI | Tumor presence | Frequency | Percentage | Gall size (mm) [a] |
|---|---|---|---|---|
| 3 | 1 | 318 | 22.52 | 5.69 (0.19) |
|   | 0 | 1094 | 77.48 |  |
| 5 | 1 | 677 | 47.95 | 6.72 (0.26) |
|   | 0 | 735 | 52.05 |  |
| 7 | 1 | 790 | 55.95 | 8.13 (0.31) |
|   | 0 | 622 | 44.05 |  |
| 9 | 1 | 894 | 63.31 | 10.02 (0.35) |
|   | 0 | 518 | 36.69 |  |
| 11 | 1 | 925 | 65.51 | 11.01 (0.36) |
|   | 0 | 487 | 34.49 |  |
| 14 | 1 | 928 | 65.72 | 14.66 (0.43) |
|   | 0 | 484 | 34.28 |  |

[a] Means and standard errors for gall size. Plants not showing tumors were excluded from the calculations.

Arabinogalactan, AtAGP17, Celluloseynthase-like, CslB-05, Celluloseynthase-like, Cs1A-09, defense, Reticulons, BTI1(AtRTNLB1), BTI2, (AtRTNLB2), BTI3, (AtRTNLB4), Rab8, GTPase, Microtubules, kinesin, Myosin, Actin, Cyclophilin, Importin, Transportin, CAK2Ms, When looking at the parameter estimates from the mixed model, gall size increased significantly in time with an average increase of 0.76 mm per week (Table 2) and based on visual inspection the tumor growth rates did not differ substantially between individual plants.

TABLE 2

Parameter estimates of fixed effects

| Parameter | Gall Size (mm) | | Weeks until tumor | |
| --- | --- | --- | --- | --- |
| | Estimate +/− Standard Error | T value | Estimate +/− Standard Error | T value |
| Intercept | 0.29 (0.42) | 0.66 | 12.49 (0.53) | 23.33 |
| WAI | 0.76 (0.02) | 50.07 | | |

For both traits, block effects explained very little variance (<1%,Table 3) or both gall size and weeks until tumor development. Broad sense heritability ranged from 0.67 for gall size to 0.41 for weeks until tumor development (Table 3).

TABLE 3

Variance components for random effects.

| Trait | Variance component | Explained variance | Percentage variance explained |
| --- | --- | --- | --- |
| Gall size | Genotype | 53.74 (4.1) | 66.74[a] |
| | Block | 0.14 (0.2) | 0.18 |
| | Residual | 26.64 (0.41) | 33.09 |
| Weeks.till.tumor | Genotype | 35.29 (3.63) | 40.80[a] |
| | Block | 0.18 (0.29) | 0.21 |
| | Residual | 51.03 (2.2) | 59.00 |

[a]Broad sense heritability

The distributions of the corrected phenotypes were very different for the two traits. Gall size showed a bimodal distribution and the parents have contrasting extreme trait values, whereas for weeks until tumor a multimodal distribution was observed. For Gall size the mode with the smallest gall sizes contained the largest number of individuals (83% if using a cutoff of 5, 72% if using a cutoff of 0).

The distribution of gall size is compatible with a scenario where a single gene underlies resistance, that this gene is dominant and the resistant parent harbours 2 copies of the resistance allele but that penetrance of the resistance alleles is not complete. Mean gall size (14WAI) for accessions with a corrected phenotype for gall size of 5 or smaller was 2.4 mm, whereas mean gall size (14 WAI) for accessions with a corrected phenotype higher than 5 was 20.8 mm.

Genomic heritability (a proxy for the narrow sense heritability) for the corrected phenotypes for gall size and weeks until tumor development were 0.57 and 0.51 respectively. This indicates that genetics explains part of the differences between individuals, but that other unknown factors e.g. the environment, also explain a proportion of the phenotypic variance. The genomic heritability provides an upper bound for the variance that can be explained by genome-wide significant markers.

Using the mixed model SNPs on three linkage groups were significant after Bonferroni correction for multiple testing (threshold for significance $1.07*10^{-6}$): on LG1, LG5 and LG7. The most significant SNPs on LG7 explained up to 53% of the phenotypic variance whereas the most significant SNPs on the other two LGs (LG1 and LG5) explained only 16% of the phenotypic variance (using linear regressions).

Looking at the allelic dosage at significant SNPs the SNPs on LG1 and LG5 co-segregate, indicating that these should be mapped to the same LG. The fact that using multiple regression only one of the three markers on LG1 and LG5 remains significant corroborates this notion. The allelic substation effects showed that three genotype classes were observed in the F1 for the most significant SNP AX-86888149 (Table 4) and that plants scoring a 2 or a 3 had almost but not entirely equally small gall sizes and that plants scoring a 4 had substantially larger gall sizes. This scenario is incompatible with both additivity and complete dominance but is compatible with incomplete dominance.

TABLE 4

Mean and standard errors for gall size per genotype for AX-86888149.

| Trait | Genotype | Mean trait score (mm) | Standard error | Number of observations | Number/ percentage of symptomless accessions[a] | Number/ percentage of symptomless accessions[b] |
| --- | --- | --- | --- | --- | --- | --- |
| Gall size in Wk 14 | 2 | 2.21 | 0.54 | 31 | 10 (32.26%) | 91 (73.39%) |
| | 3 | 6.37 | 0.45 | 217 | 18 (8.29%) | 308 (35.48%) |
| | 4 | 29.34 | 1.23 | 50 | 0 (0%) | 21 (10.5%) |
| | F1 Mean | 9.79 | 0.64 | 298 | | |

TABLE 4-continued

Mean and standard errors for gall size per genotype for AX-86888149.

| Trait | Genotype | Mean trait score (mm) | Standard error | Number of observations | Number/ percentage of symptomless accessions[a] | Number/ percentage of symptomless accessions[b] |
|---|---|---|---|---|---|---|
| Corrected gall size | 2 | −4.46 | 0.22 | 31 | | |
| | 3 | −2.47 | 0.23 | 217 | | |
| | 4 | 13.14 | 0.87 | 50 | | |
| | F1 Mean | −0.06 | 0.41 | 298 | | |

[a] Numbers are shown only for accessions for which all reps were symptomless 14WAI
[b] Numbers are shown for all individual plants harbouring the specified genotype In the QTL region LG7 (between 56 and 58.5 Mb) five resistance genes were found (Table 5).

TABLE 5

Resistance genes involved in Agrobacterium resistance near QTL peak on LG7

| Gene | LG | Start position | End position | EuGene gene prediction |
|---|---|---|---|---|
| RchiOBHmChr7g0232831 | 7 | 57010720 | 57017672 | product = Putative transcription factor WRKY family |
| RchiOBHmChr7g0232901 | 7 | 57087871 | 57092473 | product = Putative P-loop containing nucleoside triphosphate hydrolase leucine-rich repeat domain |
| RchiOBHmChr7g0232931 | 7 | 57128076 | 57131496 | product = Putative P-loop containing nucleoside triphosphate hydrolase leucine-rich repeat domain |
| RchiOBHmChr7g0232961 | 7 | 57174178 | 57174936 | product = Putative leucine-rich repeat domain L domain-containing protein |
| RchiOBHmChr7g0232471 | 7 | 56575965 | 56579420 | Putative protein kinase RLK-Pelle-LRR-XI-1 family |

The invention claimed is:

1. An *Agrobacterium tumefaciens* resistant rose plant, wherein said *Agrobacterium tumefaciens* resistance is provided by one or more genes located in linkage group 7 (LG7) between 56 to 58.5 Mb, wherein seed representative of the one or more genes located in LG7 between 56 to 58.5 Mb has been deposited with NCIMB under Accession No. 43507.

2. The *Agrobacterium tumefaciens* resistant rose plant according to claim 1, wherein said *Agrobacterium tumefaciens* resistance is provided by one or more genes located in linkage group 7 (LG7) between 56 to 58.5 Mb comprising one or more sequences selected from the group consisting of SEQ ID NOS: 11 to 14.

3. The *Agrobacterium tumefaciens* resistant rose plant according to claim 1, wherein said one or more genes located in linkage group 7 (LG7) between 56 to 58.5 Mb is a gene encoding the cDNA sequence of SEQ ID NO: 6, wherein the cDNA sequence of SEQ ID NO: 6 comprises SEQ ID NO: 11.

4. The *Agrobacterium tumefaciens* resistant rose plant according to claim 1, wherein said one or more genes located in linkage group 7 (LG7) between 56 to 58.5 Mb is a gene encoding the cDNA sequence of SEQ ID NO: 7, wherein the cDNA sequence of SEQ ID NO: 7 comprises SEQ ID NO: 12.

5. The *Agrobacterium tumefaciens* resistant rose plant according to claim 1, wherein said one or more genes located in linkage group 7 (LG7) between 56 to 58.5 Mb is a gene encoding the cDNA sequence of SEQ ID NO: 9, wherein the cDNA sequence of SEQ ID NO: 9 comprises SEQ ID NO: 13.

6. The *Agrobacterium tumefaciens* resistant rose plant according to claim 1, wherein said one or more genes located in linkage group 7 (LG7) between 56 to 58.5 Mb is a gene encoding the cDNA sequence of SEQ ID NO: 10, wherein the cDNA sequence of SEQ ID NO: 10 comprises SEQ ID NO: 14.

7. The *Agrobacterium tumefaciens* resistant rose plant according to claim 1, wherein said one or more genes located in linkage group 7 (LG7) between 56 to 58.5 Mb is a gene encoding the cDNA sequence of SEQ ID NO: 1.

8. The *Agrobacterium tumefaciens* resistant rose plant according to claim 1, wherein said one or more genes located in linkage group 7 (LG7) between 56 to 58.5 Mb is a gene encoding the cDNA sequence of SEQ ID NO: 2.

9. The *Agrobacterium tumefaciens* resistant rose plant according to claim 1, wherein said one or more genes located in linkage group 7 (LG7) between 56 to 58.5 Mb is a gene encoding the cDNA sequence of SEQ ID NO: 3.

10. The *Agrobacterium tumefaciens* resistant rose plant according to claim 1, wherein said one or more genes located in linkage group 7 (LG7) between 56 to 58.5 Mb is a gene encoding the cDNA sequence of SEQ ID NO: 4.

11. The *Agrobacterium tumefaciens* resistant rose plant according to claim 1, wherein said one or more genes located in linkage group 7 (LG7) between 56 to 58.5 Mb is a gene encoding the cDNA sequence of SEQ ID NO: 5.

12. The *Agrobacterium tumefaciens* resistant rose plant according to claim 1, wherein said rose is a hybrid.

13. The *Agrobacterium tumefaciens* resistant rose plant according to claim 1, wherein said rose plant comprises at least 2 copies of said one or more genes providing *Agrobacterium tumefaciens* resistance.

14. The *Agrobacterium tumefaciens* resistant rose plant according to claim 1, wherein said rose plant comprises a tetraploid genome and at least 3 copies of said one or more genes providing *Agrobacterium tumefaciens* resistance.

15. The *Agrobacterium tumefaciens* resistant rose plant according to claim 1, wherein said one or more genes located in linkage group 7 (LG7) between 56 to 58.5 Mb are a gene encoding the cDNA sequence of SEQ ID NO: 1 and a gene encoding the cDNA sequence of SEQ ID NO: 2; or a gene comprising SEQ ID NO: 11 and a gene comprising SEQ ID NO: 12.

16. The *Agrobacterium tumefaciens* resistant rose plant according to claim 1, wherein said one or more genes located in linkage group 7 (LG7) between 56 to 58.5 Mb are a gene encoding the cDNA sequence of SEQ ID NO: 1; a gene encoding the cDNA sequence of SEQ ID NO: 2 and a gene encoding the cDNA sequence of SEQ ID NO: 3; or a gene of comprising SEQ ID NO: 11, a gene comprising SEQ ID NO: 12 and a gene comprising SEQ ID NO: 3.

17. The *Agrobacterium tumefaciens* resistant rose plant according to claim 1, wherein said one or more genes located in linkage group 7 (LG7) between 56 to 58.5 Mb are a gene encoding the cDNA sequence of SEQ ID NO: 1; a gene encoding the cDNA sequence of SEQ ID NO: 2, a gene encoding the cDNA sequence of SEQ ID NO: 3 and a gene encoding the cDNA sequence of SEQ ID NO: 4; or a gene comprising SEQ ID NO: 11, a gene comprising SEQ ID NO: 12, a gene comprising SEQ ID NO: 13 and a gene comprising SEQ ID NO: 3.

18. The *Agrobacterium tumefaciens* resistant rose plant according to claim 1, wherein said one or more genes located in linkage group 7 (LG7) between 56 to 58.5 Mb are a gene encoding the cDNA sequence of SEQ ID NO: 1; a gene encoding the cDNA sequence of SEQ ID NO: 2, a gene encoding the cDNA sequence of SEQ ID NO: 3, a gene encoding the cDNA sequence of SEQ ID NO: 4 and a gene encoding the cDNA sequence of SEQ ID NO: 5; or a gene comprising SEQ ID NO: 11, a gene comprising SEQ ID NO: 12, a gene comprising SEQ ID NO: 14 and a gene comprising SEQ ID NO: 3.

19. A plant part, cell or reproductive tissue of an *Agrobacterium tumefaciens* resistant rose plant according to claim 1.

* * * * *

SEQUENCE LISTING

<160> NUMBER OF SEQ ID NOS: 14

<210> SEQ ID NO 1
<211> LENGTH: 2664
<212> TYPE: DNA
<213> ORGANISM: Rosa

<400> SEQUENCE: 1

```
atggagtctt tgattgtatc cccgctgctg cagctgctct ttagaaggtt gactgacact      60
gttgttgttg gtcaagtgcg aactcgcaga gagttcagga cggagatcga gaagatgcag     120
gagacgttac cgatgattaa ggcggtgata aagatgcag aggagcagca gaggaaaaat     180
cagagggtga aggcttggct ggtaaagctc aaagacgtcg cagtcgatgc tgataatctg     240
cttgatgagg ttgccaccct agttctgcgc aagcatttga tgaaagagga attttgccgt     300
ttatatgctt ccgaccgata tcgctctcga catccatctt cgtgctccag aatactgtat     360
gattgccaac atcgtgaatt tctttcttca cgtacgaatc tgaacagcaa ggacaggatt     420
ggcatgatgg tgagaaagat tggaaagcgg acaagatatg aggtaaggaa aacttgctta     480
actcttgaat tgatttctac ttaccgtaag aagtcacgca aactaaagga gcttcgtgca     540
agattggatg atgtagccaa ggagatgtct agtttccact tcaaagaaac tcagtcttat     600
ggacggtcaa gtacaatgga gagacgccaa actggaccct ctgtcaatga ttcaaaggtt     660
```

```
tatggcagag aagaggatgt ggataaaatt gtggggatgc tattgtcttc cagtagtggt    720
cctgaagttg cagtaattcc cattgttgga cttgcaggga tggggaaaac aacacttgct    780
cagttagtct acaatgatct gagggttaca agccactttc aatcttcaat atgggtgtct    840
gtcaatgata attttaaccc ggcaaggatc ataaatcaaa tgttgagtta tgtcggaaag    900
ggctgccatg actcgtttca gattgggta ctgcaatctc aattgagaga atcgttactg    960
ggaaaaaggt acttgatagt gctcgatgat gtgtggaatg aggatccaga tgaatgggat   1020
aaagtaatga atccattgaa aggctcccca ggtggaagta aaattatact aaccacccgg   1080
aataagccag ttgcagccat aactagcaca tttcccccat ttcatttgga accactgaga   1140
aaagaagagt gctggaagtt gttcaagcac cgagcctttg cagatggaac agagggtgat   1200
tttccgagac tactgcagat tggtgagaaa atagtagaca agtgcaaagg tgtcccgttg   1260
gttgcaaata ttcttggaat catgctgcgc tttaaaagag aagaaagcga gtggttacat   1320
gtgcaaagga gtgaactatg gagtattgat gcaggtgaga acagaattct atccatcttc   1380
aggctgagtt acaatcattt gccatcgcat ctgaaagctt gctttgcata ttgttcaata   1440
ttcccaaaga attatgagat taataaggaa atgttgatcc atcaatggct cgcacatggc   1500
ttaattcctc atattgtgga gtcttcaatt aggccagagg cactggcaa tgagtatttt   1560 aacaatttgt tgatgatgtt cttcttccaa gaaataaaaa aatatgatgg cagaggtatg   1620
acagaattta aaatgcatga tcatattaat gatcttgcaa atctgttgc tggagaggaa   1680 tccttgactc tagaacagga aaatgtgcac tgtagtctct caaagacatg tcatatatca   1740
gttgtttgca gttctagctc tgctttgatc cctgaagcct tgtgtaaagc aaagagattg   1800 cgaacccta atttcctttc accaagagag gattatgtgg aagccattcc aaccatacaa   1860 gcaacttta aacacctcag aatgctgaat ttcagtggat ttggaattaa gaggcttcac   1920
ccagagattg gtgggctact atccttgcgg tatcttgatc tttcaaatac tctcctagag   1980
acattgccag cgactatctg tgatctatgc aatttgcaga cattaaatct ctcaagttgt   2040
agtgagctca gggagttacc gagtggtact accaagttaa taaatctgag acatcttaac   2100
atagatgatt gtccaagact tgctagcatg cccccatcaa tgagtatgct acgacaactt   2160
caaactttgc cggtatatat catcggccgc aaccctgaaa cttctattgc tcagcttgta   2220
tcaatgacaa atctacgagg gaagttaaaa ctcaaatgtc tggaggaggc taaaagtcca   2280
cgtgacgttg tcatgataac agaatggatg aaaacgaaag aattctattc attggaactg   2340
ttgtggcaaa atgatgatga gtgcaagcta gatcataaca gatctaggca agctcgcagg   2400
caaattgatg ataaaattga ttttattctg gtagattctt taactttatc tccctttgta   2460
aggatgttgt caataaatgg ttattcagga accaagttcc cagatgagat gagttgctct   2520
cagaacttga ccgagctaaa cataataaat tgcagaagat gtgaaagtct tcctccgctc   2580
ggtcaactcc ctgtcctcaa gatcctcaac atccaaggaa tgcataatgt agtctgcatt   2640
gctatccctt atagattttc ctga                                           2664

<210> SEQ ID NO 2
<211> LENGTH: 4248
<212> TYPE: DNA
<213> ORGANISM: Rosa

<400> SEQUENCE: 2
atggattctc atctgcatca ggtgggacga ctattatccg ctgctcctga tgatgttgcc     60
```

-continued

```
tatgttggaa tctggggaat gggggcttg ggtaaaacaa ccattgccag ggctgtttat    120
tacaaaattt ctcatcaatt tgatcaccgt tgcttttggg aaaatgtgag ggaaggcttt    180
agcagttacg gtcaagtaca aatgcaactt caatttctat ctggaatctt taagggaata    240
gtcaacagtt tcgatggggg ttacatgact atgttggaaa ggctaagtcg gataaaaatt    300
ctagttgttc tcgacgatgt atcccgttcc ttggaaattg atgccttact cggaagccca    360
caggaacgtt cacttggttg tggtagtaaa gtcattgtaa caactagaga tgaacaagta    420
ctaggtggat ttaggaaata caagcccaag ccattaagtg atcctgacgc tcttgaactc    480
ttcaaccaga atgccttcag aaaaatgcca ccctcagaag agtacgttca tctctcaaga    540
cgtgcaatca aatatgctca cggtctgcct ttagcactta aaacctgggg agctcatctt    600
cgtgacagaa gtccatctgt gtggaaagat gagttggaga aaataaagaa atcccagac    660 ctagatattc accacgtgca ccatgtgctt agaagaagct ttgatggact agatgagtac    720
caaaagaaca tatttctaga tatcgcatgt tttttcaaag gaatgcacat agagtatgta    780
gaaattattc tgaacagttg tggcttcttt gccagcagtg gtttaagcgt tctaattgac    840
agagctcttg taagtatctc aaggtttggt gagctcgaga tacatgattt cctacaggaa    900
attggtaggg atatcgtctg caaagaacct tggaagcata gtagattatg gagttatgaa    960
gatgttcagg ataccttaac acaaaataag gctatggaag ttgaaggcgt aatgattgaa   1020
ttgtctgact caaagatat acgtgtagat gctcaagctt ttttcgtat gatgaacctg    1080 agattgctca gaatcactta ccccccatat gtgaacccgt taattgagat cagaaaactt   1140
tttgaagggg aattatggcc ggagcggata tacggttacc taccaaattt cgacggtaaa   1200
ttacacttga atggggacct aaagtttctt tctcataagt tgagggttct cgcttggcat   1260
ggttgccccg taaaaacttt gccgtccaac ttttacccaa agtgtcttgt tgaccttgac   1320
atgcgtcata gccacatcga acagctttgg caagaaccca aggctgcgaa agaattgata   1380
agcatcaatt taagttcctg taaaaatctt aaggaaatcc ccctctgcac tgaggcgccg   1440
aagcttcaga aactaattct taactattgt acaagtttag tggaggtttc cccatccatt   1500
tcagctctta caggccttgt tttcttgagt ttatatggtt gcactgaact taagagtctt   1560
ccaagcaaca ttcatatgat gaaatttctc aagacccttg ttctttccgg ctgctcaaat   1620
cttgagatgt ttcccgagat ttcagaagat atggaggcac tatcggagct taggttagat   1680
cgcactgcga ttaagaaact accatcctca attgaacggc ttcggggact aaatcccctt   1740
gatctttacg gctgctcaaa tcttgagatg tttcccgaga tttcagaaga tatggggca   1800 ctatcggagc ttatgttaga tggcagtgca attaaggaaa taccatcctc aattgaacgg   1860
cttcggggac ttaaatcatt aagtatgaaa aactgcacaa gccttgtctg tcttcccgac   1920
agtatctgta atttggcaga ccttacatat ctctacctcg aagggtgctc aaaactttgc   1980
aacttgcctg agaatttggg gaatttaaaa tctctgtgtg aacttaaagt agaggatact   2040
ggtataaaac gactcccggc ctgtatcttg catttgaagc ttggaagatt aaagtttcat   2100
tattgcaaac aaatggaagc ccccctttca tcatggccat catcgattga agatcgttgt   2160
actgttgtgg tgcatcttga ttttagttat tgcaatctga aggtgttatc ggatgccatt   2220 gcttatttc gttcattaaa agtattgaat ttatcaagaa ataacaatct gaagagcttg   2280
cctgcagcca tgaatcaact gggttactta gaacggcttc aattggaaga ttgcaagaga   2340
ctgagatcaa taccagagct ttcatcaaga ataagttgca taaatgcgca taattgcaca   2400
gctttggaag ctgtttcaac accacagtct ccctacgata tcggtcgatg cttcatatt   2460
```

| | | | | |
|---|---|---|---|---|
| tctaattgca | gtcagctgat | acagagagat | tttttcagag | atattgtaga aactcatttc | 2520 |
| cctcctcagg | gtaattgttc | ccgacccttt | tatttctcca | ttcctggaac tgaaattcca | 2580 |
| gagcagttca | tccatcaggg | taggggtct | tccgtaactg | cccagctacc acaaaattgg | 2640 |
| tttcacagca | acaagttttt | ggggttcgct | atttgcgcgg | ttactaatca gccccagggt | 2700 |
| gttgattatt | ggaaactgtc | tgctcgatgt | ttctgtacct | tcaaggaga tcattgcgag | 2760 |
| taccgtttca | gtttctcttt | gttcaatatt | tattttgacg | gtttctaccg cgactggctt | 2820 |
| gtgtcaaatc | acatgttagt | gggatatgtg | ccatggtctg | aatttggcat taatggagag | 2880 |
| gaagtgaatg | aacgccatta | cactgaggcc | aaatttgaga | tagaattatt gcaccgtgaa | 2940 |
| acattggagg | aagacggggt | actattcgac | ccttgcatcg | aaaggtgtga cccttgcatc | 3000 |
| gaaaggtgtg | gagttcgatt | cgttttgcc | aacaacgagg | atgaggaagt tgcccatcaa | 3060 |
| gattttgggg | aaccaatggt | acaaggtgat | aattctgaga | tcaggagcct tgagggctgc | 3120 |
| tcagctgaac | gcagtggtag | tgacatcaca | agtgacacct | ctgatgagga ggagcaatac | 3180 |
| cttaaattat | cggaagtttt | tgaaggtgca | acagagaac | cgagttacat cagaaatgag | 3240 |
| gacaatgaat | catctcggaa | gaggaaaact | ctggaaagtt | ggacacaaga agtcagagtt | 3300 |
| acatcgggtc | tgatgcaagg | ggacctggat | gatggttta | actggttctg ccataacaga | 3360 |
| catttaatcc | ctgacaaagg | aactacggat | ttaagatgcg | ggtatgtttg tacacatcga | 3420 |
| cccggctgtt | gggccagagc | taatgtgcga | tctttcattg | acgacctaac aatccttgaa | 3480 |
| attacttaca | ttgggaggca | cacttgttgg | aaaactcttc | caatgccaat gttgacacac | 3540 |
| caagtaagag | ttacaacagg | tatggagact | gaaggtcctt | ctgatggctt taggtgggtg | 3600 |
| aagtatgccc | aaacagacat | accaggagct | aaatccccaa | gagtctatta tgtatgttct | 3660 |
| cctcaaaatg | tcggaggctg | catggcaata | aaggaagtac | agcgctccaa tgataaagaa | 3720 |
| atccttcaaa | ttacttacat | aggaaggcac | acatgtacac | tagcctccac cagcaatgga | 3780 |
| ggaagggttg | atagcagtac | ctccgcggcc | aatggtgcat | cgagtgttca tgaccaagtt | 3840 |
| gtccaatcac | caagttcacc | aggagccaat | ggtcatggag | aaatgtaac cagagtagcc | 3900 |
| gacaatcctg | ttaatgacaa | caatatgatc | gtgttacaag | atgcaagctc acaggatatg | 3960 |
| gaaccgacac | cctcaaatgt | tgcaagtgtt | tcatctcaac | cagtgatctc atcaccatct | 4020 |
| ctgactcaag | ttaaccttca | acctcagtct | tgttcgcagc | ccattgttat aagatcatct | 4080 |
| cctaattcca | gaacaattgt | atctcccaac | acagggatgt | taatgaagac caagtcagta | 4140 |
| gcacagaagg | ctaaacccat | gcctaaacct | gtgacaaaaa | ccagcacaag agcaagagcc | 4200 |
| caacaaggac | caaaggagga | ttccgacaac | aaaatgtgga | agccctga | 4248 |

<210> SEQ ID NO 3
<211> LENGTH: 3777
<212> TYPE: DNA
<213> ORGANISM: Rosa

<400> SEQUENCE: 3

| | | | | |
|---|---|---|---|---|
| atgcagcaga | cgttgcagcg | gattagagcg | gcgatagaag | atgcagagga gcggcagagg | 60 |
| aaaagtgata | gggtgaagga | tttgctgata | aatctcaaag | caatcgcagt cgatgctggt | 120 |
| aatctgcttg | atgaggttgc | caccctagtt | ctgcgaaagc | aattgatgaa agaggaatct | 180 |
| cacggactac | gtgctgccac | taagaaagac | ttatttagac | tacgttacca atgcaacatg | 240 |
| tccagggtta | ttcacacacc | aggtgctcag | accagatatc | tcatattcaa gcttttgaa | 300 |

-continued

```
gcacaagaag agtttgacaa cgacattatt caagggatac tgcttcatct aggaattggt      360
gagctgcaga gtactaaaat actggcagac tttcaaagtg ccccacttgc cagtggaaag      420
ggaagtaagc agatgtatct aacgagggta gtttattatg agctttatct ttcacgtccg      480
aaggacagga ttggtgtgat aatgagagag attggagagc gtacaaaata tgaggtaagg      540
aaaacttgct taactcttga gtcgatttct acttaccgta agaagtcacg cagactaaag      600
gagcttaacg caagatggaa tgatgtagac aaggaaatgt ctaggttcca gttcaaaaaa      660
actgagtctt atagacggtc aactaccagg gagagacgag aaactggacc ctttcccaat      720
gagtcaatgg tctatggcag agaagaggat gtgaataaga ttgtgcggat gctattgtct      780
tccagtagtg gtcctgaagt tgcagtaatt cccattgttg gaattggagg gatgggaaaa      840
acaacacttg ctcagttagt ctacaatgat ccgagggtta caagccactt tcaatctttg      900
atgtgggtgt ctgtcaatgg taagtttaac ccggcagaga tcataaatca aatgttgagt      960
tatgtcagag agggcagcca tgacctgttt cagattgggt tgctgcaatc tcaattgaga     1020
gagtccttac tgggaagaag atacttaata gtgcttgatg atgtgtggaa tgtggatgaa     1080
gatgaatggg ataaagtaat gaatccattg aaaggctccg agggtggaag taaaattata     1140
ttaaccacct ggaatgaggc ggttgcagac ataactagga catttccctc ttttcgtttg     1200
gaaccactaa gaaaagaaga gtgctggaag ttgttcaagc accgagcctt gcagatgga     1260 acagaggatg attttccgag gctactgcag atcggtgaga aatagtaga caagtgccaa     1320 ggtgtcccat tgttgcaaaa tatgcttgga atcatgctgc gctttaaaag agaagcaaac     1380
gattggttac atgtgcaaga aagtgaacta tggagtattg atgcaggtga aaacagaatt     1440
ctatccatct acaggctgat ttacaatcat ttgccattgc atctgatagc ttgctttgca     1500
tattgttcaa tattcccaaa gaattatgag attaataagg aaaagttgat ccatcaatgg     1560
ctcgcacatg gcttaattcc ttataattca gggtcttcat ttgagctgga ggacattggc     1620
aatgagtatt ttaaggattt actaatgatg tctttcttcc aagaagtaag aaaacctgat     1680
gacagaggta tggcagaatt taagatgcat gatcttatta tgatcttgc aaaatcagta     1740 gctggtgagaa aattcttgac tctgggagag gaatcctcga ctctaggaca ggatattctc     1800
tcaaagacat gtcatgcatc agttgtttgc agttctagct ctattttgac ccctgaagcc     1860
ttgtgtgaag caaagagatt gcaaacccct caatttcctgt caccaagaga ggattatatg     1920
gaagccattc caaccgtact agcaactttc aaacatctca gaatgctgaa tttcagtgga     1980
tctggaatta agagtctcca ccaagagatt ggtgggctac tgtccttgcg gtatcttgat     2040
ctatcaaata ctctcctaga gacgatgcca gcgactatct gtggtctgtg caatttgcag     2100
accctgaatc tctcaagttg tattgagctc aaggagttac aagtggtac taccaagtta     2160 ataaatctga gacatctgaa catagatgat tgtccaagac ttgctggcat gcccccatcc     2220
atgggaattt tacgacgact tcaaactttg ccggtatata tcgtcggccc caactttgaa     2280
acttctattt ttcagctctc atcaatgaat ctacgaggga gttaaaaact caaatgtctg     2340
gaggatgcta aaattccgtc tgggaacaac atgattaaag tatggatgaa acgagagaa     2400 ttttcttcat tggaactgtt gtggcaaaat gacgggtgca agctagatca taacagatct     2460
aggcaagctg gcaggcaagt tgatggtcaa actgatctta ttctggtgga ttctttgact     2520
gtatcgccct ctataaaaaa gttgtcaata aatggttatt ctggaaccaa gttcccagag     2580
gagatgagtt ggcctcggaa cttgactgag ctaaatataa ttaattgcag aagatgtgaa     2640
agtcttcctc cactcggtca acttcctgtc ctgaagatcc tcaacatcca aggaatggat     2700
```

```
tctgttgtgc gcattggtgt cgaattctct ggtgaaggtg acagaccgtt tagttctctt    2760
aaagagctat ccctcaaaga ctttcctgaa ttaagaactt ggcgtagtat tgattccgga    2820
gaagtattta cttgcctgga aaaacttatt atcacaaatt gtccttttt gacaaccatg     2880 ccatggtttc cacatctccg agacttgaag ctgagcaagt gcatgcagct tgacttagta    2940
tggtcagtat caaagcttac cacactctct actcttgtta ttgactcctt tccacagttg    3000
agctttctac caaaaaatt ggtgcaaaac aattcacatc tgatatcatt aactgttact     3060
tcctgcccca atattagctc actacctgaa atctgggaa acctcactgc tctgaaatcg     3120
ctgaaaattg aatggtgtca cgggctagat actttgccaa gtggactaaa gtacctcact    3180
tcactggaga acttggaaat agttgattgt cgtggtttaa tctgtttgcc agaggaaggc    3240
atggaaggct tgtgctcact tcggtcattt tcaattgaga actgtttgaa cttaacctct    3300
ttgcctatgg ggatgaaaaa cctcacatcc cttgagaacc tcatgcttat gtgtttaaat    3360
ctggttcatc taccagagat tttcaatac ctcttggcac ttagaagcct gacgattaga     3420
agctgtgaag agcttacaag tctgccggtg ggactgcaac atgtccagaa tttacaattc    3480
ttggaaattc atcgctgccc gaaactgatg gaattgcctg agtgggtgga gcatcttgtt    3540
tcacttcgtt ccttgaaaat cttagactgc cgagaaataa agttcttgcc aaaaggtcta    3600
caatgtcttg gagcgctcca tcacctgtcc ataattgact gtcctgtcct tgagaagcgc    3660
tgcgagatga aaactggtga ggactggcag aagatatctc atattccata taaacatttt    3720
ggatcatcag cagtgcagca caggcaagac attgcatcca ccacacagaa tccttag       3777

<210> SEQ ID NO 4
<211> LENGTH: 1359
<212> TYPE: DNA
<213> ORGANISM: Rosa

<400> SEQUENCE: 4
ggagccacta acaaaaaaag agtgctagaa gttgttcaag caccgagcct ttgcagatgg      60
aacagaggac ggttttccga gccttctgcg catcgttgaa caaatagtag acaagtgcaa     120
aagtgtccca ttggttgcaa atattcttgg aagcatgctg cgctttaaaa gagaagaaag    180
cgagtggtta catgtgcaaa ggagtgaact atggagtatt gatgcagggg agaacagaat    240
tctgtccatc ttaagggtaa gttacaatca tttgccattg catctgaaag cttgctttgc    300
atattgttca gtattcccaa agaattatga gattaataag gaaaagttga tccatcaata    360
gctcgcacat ggcttaattc ctcatagtag aaactcttca gttaggccgg aggacattgg    420
caatgagtat tttaacaatt tattaatgat gtctttcttc caagaaataa gaaaatttga    480
tgacagaggt atggcagaat ttaaaatgca tgatcatatt aatgatcttg caaatctgt     540 tgctggagag gaatacttga ctctaggaca ggaaaatgtc cactatggtc tctcaaacac    600
atgtcatcag ttgtatgcag ttctagctct gctttgatcc ctgaagcctt gtgtgaagca    660
aagagattgc gaaccctcaa tttcctgtcg ccaagagagg attatatgga agccattcca    720
accatactag caactttaa acatctcaga atgctgaatt cagtggatc tggaattaag      780 agtctccacc aggagattgg tgggctaata tccttgcggt atcttgatct gtcaaatact    840
accctagaga cgatgccagc gactatctgt gatcgctgcc atttgcagac cctgaatctc    900
tcaagttgtc gtgagctcaa ggagttacca agtggtacta ccaagttaat aaatctgaga    960
catcttaaca tagatgattg tccaagactt gctggcatgc cccatcgat  gggaatttta    1020
```

| | |
|---|---|
| caacaacttc aaactttgcc agtatatatc atcggccgca attttgaaac ttctattttt | 1080 |
| cagattatct caatgaatct acgagggaag ttaaaaatca aatgtctgga ggaggctaaa | 1140 |
| attccatttg gaaacaacat gattaaaaga tggatgctaa cgaaagagtt tcagtcattg | 1200 |
| gaactgttgt ggcaaaatga tgggggcaag ctagatcata atagatctag gcaagctggc | 1260 |
| aggcaagttg atgatagaac tgaattttgt ctggtagatt ctttgactgt atcgcccttt | 1320 |
| ataagaatgt tgtcaataaa tggttattca ggaacctag | 1359 |

<210> SEQ ID NO 5
<211> LENGTH: 2955
<212> TYPE: DNA
<213> ORGANISM: Rosa

<400> SEQUENCE: 5

| | |
|---|---|
| atgccattac ccaaaaacca ccacctccat ctctacctcc tcttcttcct cttcctcctc | 60 |
| tccaacgccg ccgcagccga cgagcttcaa atcctactaa aactcaaatc ctccctccag | 120 |
| gactcgaact cccaactctt cgccacatgg gactccaccg ccaattcgtt ttgcaaattc | 180 |
| accggaatca cctgcaacga cgtcggttcg gttcgagaaa tcgaactttc gaaccagaag | 240 |
| ctgtcggggt ctcttccgct ggactccata tgccaacttc cctcattaga aaagctcgct | 300 |
| ttcgggtcca atttcctgca cggtacaatc acggaggact gagaaactg tacgaagctg | 360 |
| aaatacctgg atttggggaa aaacttgttc gcgggttcat tccctgacat atcttccttg | 420 |
| tcccaactgg agcatcttca tctgaacggc agctggtttt ccgggatttt cccgtggact | 480 |
| tccctcacca acatgactgg tctgattcgt ttgagcttgg gtgacaaccc gtttgatccc | 540 |
| agcccgtttc caaggaagt tgaaaatctt aaaaagctcg agtggctcta cttggcaaac | 600 |
| tgcagcatcc aaggaacaat accaagtgaa atcgggaact tggtcgagct tatcaacctg | 660 |
| gagttgtccg ataacaacat gaccggagaa attccggtcg agattggaca gctcaccaag | 720 |
| ctctggcagc tggagctcta catcaacagg ttcaccggaa tgcttccttt cgggctaaga | 780 |
| aacctcacca ttctcgagaa cttcgacgcc tctgagaatt ttctggaagg cgatttgaac | 840 |
| gagttgaggt ttctgaccaa cttggttttct ctgcagctgt atgacaacaa ttttttccggc | 900 |
| gaagtaccgg aagagttcgg cgaattaaac aagcttgtga atctgtcttt gtacggtaac | 960 |
| aagctgaccg tcctctgcc tcagaaattg ggttcttggt cggagatggg cttcatcgac | 1020 |
| gtgtcggaga acttcttgac cgggactatt ccgccggaca tgtgcaacaa agggacgatg | 1080 |
| aagcagctgc tcatgcttca gaacaaatta actggcgaaa ttccggcaaa ctacgccaag | 1140 |
| tgcacgacgt tgacccggtt cagggtcaac aacaactccc tctccggtgt ggttccggca | 1200 |
| ggactttggg gattgccgaa tgtggcaatc attgacatca cttcgaatca aattgaaggg | 1260 |
| ccgattactt ccgatatcgg aaacgccaag aagcttgcgc agttgtttgt gagttacaat | 1320 |
| cggttatctg gtgaattacc ggacgagctt tcgaagtcaa cttcgttggt ttcggttatg | 1380 |
| ttgaataaca atcagttttc cggtaagatt ccggcgaaga taggggactt gaagcaattg | 1440 |
| ggtactctgc atttagagag caacttgttg tcttcttcga ttcccaagtc attgggaagc | 1500 |
| tgtagtttcc tgagtgactt gaacacgcg aacaactcgc tttccggtga atcccatca | 1560 |
| tcttttgggct ctttgccgac cttgaattct ctggatttgt ctcacaacca actctccggt | 1620 |
| aaaatcccgg aaagtctagc atctctgaga ctaagcatgc ttgatctttc gcacaacaga | 1680 |
| ctgaccggtg ccgtaccgga atctctccg attgcagcct acaacggcag cctttccggt | 1740 |
| aacccgggtc tctgcagcat ggacatcacc tacttcccac ggtgctcgcc gaaaaaggaa | 1800 |

| | |
|---|---|
| atgtccgacg atgtcaggac actcattatt tgcttctcag tgggtacagc aatattgttt | 1860 |
| gtttcactca tttgcttctc gttcttaaag aggaaggaga aagatcaaga ccgttcattg | 1920 |
| aaggaagaat cttgggatgt aaagtctttc catgtaataa ccttcagtga ggatgagatt | 1980 |
| cttgattcca ttactcaaga gaatctaatt ggaaaaggag ttctggaaaa tgtctacaaa | 2040 |
| gtgtcactag ccaatggcaa agaagtcgcc gtgaagcaca tatggaacac tgatccaagc | 2100 |
| ggccggaaaa tgttcaagag caccacaccg atgctcggga cgggggcag tggtagttcg | 2160 |
| aaatcgaagg aatttgatgc tgaggtgcag acgttgagct caataaggca tgtgaatgtg | 2220 |
| gtgaagttgt tctgcagcat tactagtgag gactcgagcc ttttggtcta cgagtactta | 2280 |
| ccgaacggaa gcttgtggga tcggctgcac acgtgtgaga gatgaagct tgattgggac | 2340 |
| gcaaggtatg agattgcagt cggagcagcc aaagggttgg agtatctgca ccatggctgt | 2400 |
| gagaggctag tgattcatag agatgtcaag tcgagtaaca ttttgttaga tgagttttg | 2460 |
| aagccccgga tcgcggattt tgggctcgcc aagatggttc agactaatgc aattaaggac | 2520 |
| tcgtctcatg ttgttgctgg aacacacggt tacatagctc ctgaatatgg ttacacctac | 2580 |
| aaggtgaatg agaagagcga tgtgtatagc tttggtgtag tactaatgga gctagtgacc | 2640 |
| gggaaaaagc cgatagatcc atcctttggg gacaacaagg acatagtgaa ctggatatgt | 2700 |
| ggcaacctga gagtagaga gagcgtgtta ggtgtggtgg actcgtacgt tcctgaggcc | 2760 |
| tatagggaag aggctatcaa ggtattgaga attgcaattc tatgcacagc taggcttcca | 2820 |
| gagctaagac cttccatgag aagtgtcgtt caaatgcttg aagaagctca cgagccaatg | 2880 |
| aaattgctgg acattgttat cagcaaagat ggttctagta gaaaatgga agtacttaaa | 2940 |
| ggaacagaga agtga | 2955 |

<210> SEQ ID NO 6
<211> LENGTH: 2664
<212> TYPE: DNA
<213> ORGANISM: Rosa

<400> SEQUENCE: 6

| | |
|---|---|
| atggagtctt tgattgtatc cccgctgctg cagctgctct ttagaaggtt gactgacact | 60 |
| gttgttgttg gtcaagtgcg aactcgcaga gagttcagga cggagatcga aagatgcag | 120 |
| gagacgttac cgatgattaa ggcggtgata aagatgcag aggagcagca gaggaaaaat | 180 |
| cagagggtga aggcttggct ggtaaagctc aaagacgtcg cagtcgatgc tgataatctg | 240 |
| cttgatgagg ttgccaccct agttctgcgc aagcatttga tgaaagagga attttgccgt | 300 |
| ttatatgctt ccgaccgata tcgctctcga catccatctt cgtgctccag aatactgtat | 360 |
| gattgccaac atcgtgaatt tctttcttca cgtacgaatc tgaacagcaa ggacaggatt | 420 |
| ggcatgatgg tgagaaagat tggaaagcgg acaagatatg aggtaaggaa aacttgctta | 480 |
| actcttgaat tgatttctac ttaccgtaag aagtcacgca aactaaagga gcttcgtgca | 540 |
| agattggatg atgtagccaa ggagatgtct agtttccact tcaaagaaac tcagtcttat | 600 |
| ggacggtcaa gtacaatgga gagacgccaa actggaccct ctgtcaatga ttcaaaggtt | 660 |
| tatggcagag aagaggatgt ggataaaatt gtggggatgc tattgtcttc cagtagtggt | 720 |
| cctgaagttg cagtaattcc cattgttgga cttgcaggga tggggaaaac aacacttgct | 780 |
| cagttagtct acaatgatct gagggttaca agccactttc aatcttcaat atgggtgtct | 840 |
| gtcaatgata attttaaccc ggcaaggatc ataaatcaaa tgttgagtta tgtcggaaag | 900 |

```
ggctgccatg actcgtttca gattggggta ctgcaatctc aattgagaga atcgttactg    960
ggaaaaaggt acttgatagt gctcgatgat gtgtggaatg aggatccaga tgaatgggat   1020
aaagtaatga atccattgaa aggctcccca ggtggaagta aaattatact aaccacccgg   1080
aataagccag ttgcagccat aactagcaca tttcccccat ttcatttgga accactgaga   1140
aaagaagagt gctggaagtt gttcaagcac cgagcctttg cagatggaac agagggtgat   1200
tttccgagac tactgcagat tggtgagaaa atagtagaca agtgcaaagg tgtcccgttg   1260
gttgcaaata ttcttggaat catgctgcgc tttaaaagag aagaaagcga gtggttacat   1320
gtgcaaagga gtgaactatg gagtattgat gcaggtgaga acagaattct atccatcttc   1380
aggctgagtt acaatcattt gccatcgcat ctgaaagctt gctttgcata ttgttcaata   1440
ttcccaaaga attatgagat taataaggaa atgttgatcc atcaatggct cgcacatggc   1500
ttaattcctc atattgtgga gtcttcaatt aggccagagg acactggcaa tgagtatttt   1560
aacaatttgt tgatgatgtt cttcttccaa gaaataaaaa aatatgatgg cagaggtatg   1620
acagaattta aaatgcatga tcatattaat gatcttgcaa atctgttgc tggagaggaa    1680
tccttgactc tagaacagga aaatgtgcac tgtagtctct caaagacatg tcatatatca   1740
gttgtttgca gttctagctc tgctttgatc cctgaagcct tgtgtaaagc aaagagattg   1800
cgaacccttta atttcctttc accaagagag gattatgtgg aagccattcc aaccatacta   1860
gcaactttta aacacctcag aatgctgaat ttcagtggat ttggaattaa gaggcttcac   1920
ccagagattg gtgggctact atccttgcgg tatcttgatc tttcaaatac tctcctagag   1980
acattgccag cgactatctg tgatctatgc aatttgcaga cattaaatct ctcaagttgt   2040
agtgagctca gggagttacc gagtggtact accaagttaa taaatctgag acatcttaac   2100
atagatgatt gtccaagact tgctagcatg cccccatcaa tgagtatgct acgacaactt   2160
caaactttgc cggtatatat catcggccgc aaccctgaaa cttctattgc tcagcttgta   2220
tcaatgacaa atctacgagg gaagttaaaa ctcaaatgtc tggaggaggc taaaagtcca   2280
cgtgacgttg tcatgataac agaatggatg aaaacgaaag aattctattc attggaactg   2340
ttgtggcaaa atgatgatga gtgcaagcta gatcataaca gatctaggca agctcgcagg   2400
caaattgatg ataaaattga ttttattctg gtagattctt taactttatc tccctttgta   2460
aggatgttgt caataaatgg ttattcagga accaagttcc cagatgagat gagttgctct   2520
cagaacttga ccgagctaaa cataataaat tgcagaagat gtgaaagtct tcctccgctc   2580
ggtcaactcc ctgtcctcaa gatcctcaac atccaaggaa tgcataatgt agtctgcatt   2640
gctatccctt atagattttc ctga                                          2664

<210> SEQ ID NO 7
<211> LENGTH: 4248
<212> TYPE: DNA
<213> ORGANISM: Rosa

<400> SEQUENCE: 7
atggattctc atctgcatca ggtgggacga ctattatccg ctgctcctga tgatgttgcc     60
tatgttggaa tctggggaat gggcggcttg ggtaaaacaa ccattgccag ggctgtttat    120
tacaaaattt ctcatcaatt tgatcaccgt tgcttttttgg aaaatgtgag ggaaggcttt    180
agcagttacg gtcaagtaca aatgcaactt caatttctat ctggaatctt aagggaata    240
gtcaacagtt cgatgggggg ttacatgact atgttgaaa ggctaagtcg gataaaaatt     300
ctagttgttc tcgacgatgt atcccgttcc ttggaaattg atgccttact cggaagccca    360
```

```
caggaacgtt cacttggttg tggtagtaaa gtcattgtaa caactagaga tgaacaagta    420
ctaggtggat ttaggaaata caagcccaag ccattaagtg atcctgacgc tcttgaactc    480
ttcaaccaga atgccttcag aaaaatgcca ccctcagaag agtacgttca tctctcaaga    540
cgtgcaatca aatatgctca cggtctgcct ttagcactta aaacctgggg agctcatctt    600
cgtgacagaa gtccatctgt gtggaaagat gagttggaga aaataaagaa aatcccagac    660
ctagatattc accacgtgca ccatgtgctt agaagaagct tgatggact agatgagtac     720 caaaagaaca tatttctaga tatcgcatgt tttttcaaag gaatgcacat agagtatgta    780
gaaattattc tgaacagttg tggcttcttt gccagcagtg gtttaagcgt tctaattgac    840
agagctcttg taagtatctc aaggtttggt gagctcgaga tacatgattt cctacaggaa    900
attggtaggg atatcgtctg caaagaacct tggaagcata gtagattatg gagttatgaa    960
gatgttcagg ataccttaac acaaaataag gctatggaag ttgaaggcgt aatgattgaa    1020
ttgtctgact caaagatat acgtgtagat gctcaagctt tttttcgtat gatgaacctg     1080
agattgctca gaatcactta cccccccatat gtgaacccctt taattgagat cagaaaactt   1140
tttgaagggg aattatggcc ggagcggata tacggttacc taccaaattt cgacggtaaa    1200
ttacacttga atggggacct aaagtttctt tctcataagt tgagggttct cgcttggcat    1260
ggttgccccg taaaaacttt gccgtccaac ttttacccaa agtgtcttgt tgaccttgac    1320
atgcgtcata gccacatcga acagctttgg caagaaccca aggctgcgaa agaattgata    1380
agcatcaatt taagttcctg taaaaatctt aaggaaatcc ccctctgcac tgaggcgccg    1440
aagcttcaga aactaattct taactattgt acaagtttag tggaggtttc cccatccatt    1500
tcagctctta caggccttgt tttcttgagt ttatatggtt gcactgaact taagagtctt    1560
ccaagcaaca ttcatatgat gaaatttctc aagacccttg ttctttccgg ctgctcaaat    1620
cttgagatgt ttcccgagat ttcagaagat atggaggcac tatcggagct taggttagat    1680
cgcactgcga ttaagaaact accatcctca attgaacggc ttcggggact aaatcccctt    1740
gatctttacg gctgctcaaa tcttgagatg tttcccgaga tttcagaaga tatgggggca    1800
ctatcggagc ttatgttaga tggcagtgca attaaggaaa taccatcctc aattgaacgg    1860
cttcggggac ttaaatcatt aagtatgaaa aactgcacaa gccttgtctg tcttcccgac    1920
agtatctgta atttggcaga ccttacatat ctctacctcg aagggtgctc aaaactttgc    1980
aacttgcctg agaatttggg gaatttaaaa tctctgtgtg aacttaaagt agaggatact    2040
ggtataaaac gactcccggc ctgtatcttg catttgaagc ttggaagatt aaagtttcat    2100
tattgcaaac aaatggaagc ccccctttca tcatggccat catcgattga agatcgttgt    2160
actgttgtgg tgcatcttga ttttagttat tgcaatctga aggtgttatc ggatgccatt    2220
gcttattttc gttcattaaa agtattgaat ttatcaagaa ataacaatct gaagagcttg    2280
cctgcagcca tgaatcaact gggttactta gaacggcttc aattggaaga ttgcaagaga    2340
ctgagatcaa taccagagct ttcatcaaga ataagttgca taaatgcgca taattgcaca    2400
gctttggaag ctgttttcaac accacagtct ccctacgata tcggtcgatg cttcatatttt  2460 tctaattgca gtcagctgat acagagagat tttttcagag atattgtaga aactcatttc    2520
cctcctcagg gtaattgttc ccgacccttt tatttctcca ttcctggaac tgaaattcca    2580
gagcagttca tccatcaggg taggggtct tccgtaactg cccagctacc acaaaattgg     2640
tttcacagca acaagttttt ggggttcgct atttgcgcgg ttactaatca gccccagggt    2700
```

| | |
|---|---|
| gttgattatt ggaaactgtc tgctcgatgt ttctgtacct tcaaaggaga tcattgcgag | 2760 |
| taccgtttca gtttctcttt gttcaatatt tattttgacg gtttctaccg cgactggctt | 2820 |
| gtgtcaaatc acatgttagt gggatatgtg ccatggtctg aatttggcat taatggagag | 2880 |
| gaagtgaatg aacgccatta cactgaggcc aaatttgaga tagaattatt gcaccgtgaa | 2940 |
| acattggagg aagacggggt actattcgac ccttgcatcg aaaggtgtga cccttgcatc | 3000 |
| gaaaggtgtg gagttcgatt cgttttttgcc aacaacgagg atgaggaagt tgcccatcaa | 3060 |
| gattttgggg aaccaatggt acaaggtgat aattctgaga tcaggagcct tgagggctgc | 3120 |
| tcagctgaac gcagtggtag tgacatcaca agtgacacct ctgatgagga ggagcaatac | 3180 |
| cttaaattat cggaagtttt tgaaggtgca acagagaac cgagttacat cagaaatgag | 3240 |
| gacaatgaat catctcggaa gaggaaaact ctggaaagtt ggacacaaga agtcagagtt | 3300 |
| acatcgggtc tgatgcaagg ggacctggat gatggttttta actggttctg ccataacaga | 3360 |
| catttaatcc ctgacaaagg aactacggat ttaagatgcg ggtatgtttg tacacatcga | 3420 |
| cccggctgtt gggccagagc taatgtgcga tctttcattg acgacctaac aatccttgaa | 3480 |
| attacttaca ttgggaggca cacttgttgg aaaactcttc caatgccaat gttgacacac | 3540 |
| caagtaagag ttacaacagg tatggagact gaaggtcctt ctgatggctt taggtgggtg | 3600 |
| aagtatgccc aaacagacat accaggagct aaatccccaa gagtctatta tgtatgttct | 3660 |
| cctcaaaatg tcggaggctg catggcaata aggaagtac agcgctccaa tgataaagaa | 3720 |
| atccttcaaa ttacttacat aggaaggcac acatgtacac tagcctccac cagcaatgga | 3780 |
| ggaagggttg atagcagtac ctccgcggcc aatggtgcat cgagtgttca tgaccaagtt | 3840 |
| gtccaatcac caagttcacc aggagccaat ggtcatggag gaaatgtaac cagagtagcc | 3900 |
| gacaatcctg ttaatgacaa caatatgatc gtgttacaag atgcaagctc acaggatatg | 3960 |
| gaaccgacac cctcaaatgt tgcaagtgtt tcatctcaac cagtgatctc atcaccatct | 4020 |
| ctgactcaag ttaaccttca acctcagtct tgttcgcagc ccattgttat aagatcatct | 4080 |
| cctaattcca gaacaattgt atctcccaac acagggatgt taatgaagac caagtcagta | 4140 |
| gcacagaagg ctaaacccat gcctaaacct gtgacaaaaa ccagcacaag agcaagagcc | 4200 |
| caacaaggac caaaggagga ttccgacaac aaaatgtgga agccctga | 4248 |

<210> SEQ ID NO 8
<211> LENGTH: 3777
<212> TYPE: DNA
<213> ORGANISM: Rosa

<400> SEQUENCE: 8

| | |
|---|---|
| atgcagcaga cgttgcagcg gattagagcg gcgatagaag atgcagagga gcggcagagg | 60 |
| aaaagtgata gggtgaagga tttgctgata aatctcaaag caatcgcagt cgatgctggt | 120 |
| aatctgcttg atgaggttgc cacccctagtt ctgcgaaagc aattgatgaa agaggaatct | 180 |
| cacggactac gtgctgccac taagaaagac ttatttgac tacgttacca atgcaacatg | 240 |
| tccagggtta ttcacacacc aggtgctcag accagatatc tcatattcaa gcttttttgaa | 300 |
| gcacaagaag agtttgacaa cgacattatt caagggatac tgcttcatct aggaattggt | 360 |
| gagctgcaga gtactaaaat actggcagac tttcaaagtg ccccacttgc cagtggaaag | 420 |
| ggaagtaagc agatgtatct aacgagggta gtttattatg agctttatct ttcacgtccg | 480 |
| aaggacagga ttggtgtgat aatgagagag attggagagc gtacaaaata tgaggtaagg | 540 |
| aaaacttgct taactcttga gtcgatttct acttaccgta agaagtcacg cagactaaag | 600 |

```
gagcttaacg caagatggaa tgatgtagac aaggaaatgt ctaggttcca gttcaaaaaa    660
actgagtctt atagacggtc aactaccagg gagagacgaa aaactggacc ctttcccaat    720
gagtcaatgg tctatggcag agaagaggat gtgaataaga ttgtgcggat gctattgtct    780
tccagtagtg gtcctgaagt tgcagtaatt cccattgttg gaattggagg gatgggaaa    840
acaacacttg ctcagttagt ctacaatgat ccgagggtta caagccactt tcaatctttg    900
atgtgggtgt ctgtcaatgg taagtttaac ccggcagaga tcataaatca aatgttgagt    960
tatgtcagag agggcagcca tgacctgttt cagattgggt tgctgcaatc tcaattgaga   1020
gagtccttac tgggaagaag atacttaata gtgcttgatg atgtgtggaa tgtggatgaa   1080
gatgaatggg ataaagtaat gaatccattg aaaggctccg agggtggaag taaaattata   1140
ttaaccacct ggaatgaggc ggttgcagac ataactagga catttccctc ttttcgtttg   1200
gaaccactaa gaaaagaaga gtgctggaag ttgttcaagc accgagcctt tgcagatgga   1260
acagaggatg attttccgag gctactgcag atcggtgaga aaatagtaga caagtgccaa   1320
ggtgtcccat ttgttgcaaa tatgcttgga atcatgctgc gctttaaaag agaagcaaac   1380
gattggttac atgtgcaaga agtgaacta tggagtattg atgcaggtga aaacagaatt   1440
ctatccatct acaggctgat ttacaatcat ttgccattgc atctgatagc ttgctttgca   1500
tattgttcaa tattcccaaa gaattatgag attaataagg aaaagttgat ccatcaatgg   1560
ctcgcacatg gcttaattcc ttataattca gggtcttcat tgagctgga ggacattggc   1620
aatgagtatt ttaaggattt actaatgatg tctttcttcc aagaagtaag aaaacctgat   1680
gacagaggta tggcagaatt taagatgcat gatcttatta atgatcttgc aaaatcagta   1740
gctggtgagg aattcttgac tctgggagag gaatcctcga ctctaggaca ggatattctc   1800
tcaaagacat gtcatgcatc agttgtttgc agttctagct ctattttgac ccctgaagcc   1860
ttgtgtgaag caaagagatt gcaaaccctc aatttcctgt caccaagaga ggattatatg   1920
gaagccattc aaccgtact agcaactttc aaacatctca gaatgctgaa tttcagtgga   1980
tctggaatta agagtctcca ccaagagatt ggtgggctac tgtccttgcg gtatcttgat   2040
ctatcaaata ctctcctaga gacgatgcca gcgactatct gtggtctgtg caatttgcag   2100
accctgaatc tctcaagttg tattgagctc aaggagttac caagtggtac taccaagtta   2160
ataaatctga gacatctgaa catagatgat tgtccaagac ttgctggcat gcccccatcc   2220
atgggaattt tacgacgact tcaaactttg ccggtatata tcgtcggccc caactttgaa   2280
acttctattt tcagctctc atcaatgaat ctacgaggga agttaaaact caaatgtctg   2340
gaggatgcta aaattccgtc tgggaacaac atgattaaag tatggatgaa aacgagagaa   2400
ttttcttcat tggaactgtt gtggcaaaat gacgggtgca agctagatca taacagatct   2460
aggcaagctg gcaggcaagt tgatggtcaa actgatctta ttctggtgga ttctttgact   2520
gtatcgccct ctataaaaaa gttgtcaata aatggttatt ctggaaccaa gttcccagag   2580
gagatgagtt ggcctcggaa cttgactgag ctaaatataa ttaattgcag aagatgtgaa   2640
agtcttcctc cactcggtca acttcctgtc ctgaagatcc tcaacatcca aggaatggat   2700
tctgttgtgc gcattggtgt cgaattctct ggtgaaggtg acagaccgtt tagttctctt   2760
aaagagctat ccctcaaaga ctttcctgaa ttaagaactt ggcgtagtat tgattccgga   2820
gaagtatta cttgcctgga aaaacttatt atcacaaatt gtcctttttt gacaaccatg   2880
ccatggtttc cacatctccg agacttgaag ctgagcaagt gcatgcagct tgacttagta   2940
```

```
tggtcagtat caaagcttac cacactctct actcttgtta ttgactcctt tccacagttg    3000
agctttctac caaaaaaatt ggtgcaaaac aattcacatc tgatatcatt aactgttact    3060
tcctgcccca atattagctc actacctgaa atctgggaa acctcactgc tctgaaatcg     3120
ctgaaaattg aatggtgtca cgggctagat actttgccaa gtggactaaa gtacctcact    3180
tcactggaga acttggaaat agttgattgt cgtggtttaa tctgtttgcc agaggaaggc    3240
atggaaggct tgtgctcact tcggtcattt tcaattgaga actgtttgaa cttaacctct    3300
ttgcctatgg ggatgaaaaa cctcacatcc cttgagaacc tcatgcttat gtgtttaaat    3360
ctggttcatc taccagagat ttttcaatac ctcttggcac ttagaagcct gacgattaga    3420
agctgtgaag agcttacaag tctgccggtg ggactgcaac atgtccagaa tttacaattc    3480
ttggaaattc atcgctgccc gaaactgatg gaattgcctg agtgggtgga gcatcttgtt    3540
tcacttcgtt ccttgaaaat cttagactgc cgagaaataa agttcttgcc aaaaggtcta    3600
caatgtcttg gagcgctcca tcacctgtcc ataattgact gtcctgtcct tgagaagcgc    3660
tgcgagatga aaactggtga ggactggcag aagatatctc atattccata taaacatttt    3720
ggatcatcag cagtgcagca caggcaagac attgcatcca ccacacagaa tccttag       3777

<210> SEQ ID NO 9
<211> LENGTH: 1359
<212> TYPE: DNA
<213> ORGANISM: Rosa

<400> SEQUENCE: 9
ggagccacta acaaaaaaag agtgctagaa gttgttcaag caccgagcct ttgcagatgg      60
aacagaggac ggttttccga gccttctgcg catcgttgaa caaatagtag acaagtgcaa     120
aagtgtccca ttggttgcaa atattcttgg aagcatgctg cgctttaaaa gagaagaaag     180
cgagtggtta catgtgcaaa ggagtgaact atggagtatt gatgcagggg agaacagaat     240
tctgtccatc ttaagggtaa gttacaatca tttgccattg catctgaaag cttgctttgc     300
atattgttca gtattcccaa agaattatga gattaataag gaaaagttga tccatcaatg     360
gctcgcacat ggcttaattc ctcatagtag aaaactcttca gttaggccgg aggacattgg     420
caatgagtat tttaacaatt tattaatgat gtctttcttc caagaaataa gaaaatttga     480
tgacagaggt atggcagaat ttaaaatgca tgatcatatt aatgatcttg caaaatctgt     540
tgctggagag gaatacttga ctctaggaca ggaaaatgtc cactatggtc tctcaaacac     600
atgtcatcag ttgtatgcag ttctagctct gctttgatcc ctgaagcctt gtgtgaagca     660
aagagattgc gaaccctcaa tttcctgtcg ccaagagagg attatatgga agccattcca     720
accatactag caacttttaa acatctcaga atgctgaatt cagtggatc tggaattaag     780 agtctccacc aggagattgg tgggctaata tccttgcggt atcttgatct gtcaaatact    840
accctagaga cgatgccagc gactatctgt gatcgctgcc atttgcagac cctgaatctc    900
tcaagttgtc gtgagctcaa ggagttacca agtggtacta ccaagttaat aaatctgaga    960
catcttaaca tagatgattg tccaagactt gctggcatgc cccatcgat ggaattttta    1020 caacaacttc aaactttgcc agtatatatc atcggccgca attttgaaac ttctattttt    1080
cagattatct caatgaatct acgagggaag ttaaaaatca aatgtctgga ggaggctaaa    1140
attccatttg gaaacaacat gattaaaaga tggatgctaa cgaaagagtt tcagtcattg    1200
gaactgttgt ggcaaaatga tgggggcaag ctagatcata atagatctag gcaagctggc    1260
aggcaagttg atgatagaac tgaattttgt ctggtagatt cttttgactgt atcgcccttt    1320
```

```
ataagaatgt tgtcaataaa tggttattca ggaacctag                     1359

<210> SEQ ID NO 10
<211> LENGTH: 2955
<212> TYPE: DNA
<213> ORGANISM: Rosa

<400> SEQUENCE: 10
atgccattac ccaaaaacca ccacctccat ctctacctcc tcttcttcct cttcctcctc    60
tccaacgccg ccgcagccga cgagcttcaa atcctactaa aactcaaatc ctccctccag   120
gactcgaact cccaactctt cgccacatgg gactccaccg ccaattcgtt ttgcaaattc   180
accggaatca cctgcaacga cgtcggttcg gttcgagaaa tcgaactttc gaaccagaag   240
ctgtcggggt ctcttccgct ggactccata tgccaacttc cctcattaga aaagctcgct   300
ttcgggtcca atttcctgca cggtacaatc acggaggact gagaaactg tacgaagctg   360
aaatacctgg atttggggaa aaacttgttc gcgggttcat ccctgacat atcttccttg   420
tcccaactgg agcatcttca tctgaacggc agctggtttt ccggattttt cccgtggact   480
tccctcacca acatgactgg tctgattcgt ttgagcttgg gtgacaaccc gtttgatccc   540
agcccgtttc caaggaagt tgaaaatctt aaaaagctcg agtggctcta cttggcaaac   600
tgcagcatcc aaggaacaat accaagtgaa atcgggaact ggtcgagct tatcaacctg   660
gagttgtccg ataacaacat gaccggagaa attccggtcg agattggaca gctcaccaag   720
ctctggcagc tggagctcta catcaacagg ttcaccggaa tgcttccttt cgggctaaga   780
aacctcacca ttctcgagaa cttcgacgcc tctgagaatt ttctggaagg cgatttgaac   840
gagttgaggt ttctgaccaa cttggtttct ctgcagctgt atgacaacaa ttttttccggc   900
gaagtaccgg aagagttcgg cgaattaaag aagcttgtga atctgtcttt gtacggtaac   960
aagctgaccg tcctctgcc tcagaaattg ggttcttggt cggagatggg cttcatcgac  1020
gtgtcggaga acttcttgac cgggactatt ccgccggaca tgtgcaacaa agggacgatg  1080
aagcagctgc tcatgcttca gaacaaatta actggcgaaa ttccggcaaa ctacgccaag  1140
tgcacgacgt tgacccggtt cagggtcaac aacaactccc tctccggtgt ggttccggca  1200
ggactttggg gattgccgaa tgtggcaatc attgacatca cttcgaatca aattgaaggg  1260
ccgattactt ccgatatcgg aaacgccaag aagcttgcgc agttgtttgt gagttacaat  1320
cggttatctg gtgaattacc ggacgagctt tcgaagtcaa cttcgttggt ttcggttatg  1380
ttgaataaca atcagttttc cggtaagatt ccggcgaaga tagggggactt gaagcaattg  1440
ggtactctgc atttagagag caacttgttg tcttcttcga ttcccaagtc attgggaagc  1500
tgtagtttcc tgagtgactt gaacacggcg aacaactcgc tttccggtga atcccatca   1560
tcttttgggct ctttgccgac cttgaattct ctggatttgt ctcacaacca actctccggt  1620
aaaatcccgg aaagtctagc atctctgaga ctaagcatgc ttgatctttc gcacaacaga  1680
ctgaccggtg ccgtaccgga atctctctcg attgcagcct acaacggcag ccttccggt   1740
aacccgggtc tctgcagcat ggacatcacc tacttcccac ggtgctcgcc gaaaaaggaa  1800
atgtccgacg atgtcaggac actcattatt tgcttctcag tgggtacagc aatattgttt  1860
gtttcactca tttgcttctc gttcttaaag aggaaggaga aagatcaaga ccgttcattg  1920
aaggaagaat cttgggatgt aaagtctttc catgtaataa ccttcagtga ggatgagatt  1980
cttgattcca ttactcaaga gaatctaatt ggaaaaggag gttctggaaa tgtctacaaa  2040
```

| | |
|---|---:|
| gtgtcactag ccaatggcaa agaagtcgcc gtgaagcaca tatggaacac tgatccaagc | 2100 |
| ggccggaaaa tgttcaagag caccacaccg atgctcggga gacggggcag tggtagttcg | 2160 |
| aaatcgaagg aatttgatgc tgaggtgcag acgttgagct caataaggca tgtgaatgtg | 2220 |
| gtgaagttgt tctgcagcat tactagtgag gactcgagcc ttttggtcta cgagtactta | 2280 |
| ccgaacggaa gcttgtggga tcggctgcac acgtgtgaga agatgaagct tgattgggac | 2340 |
| gcaaggtatg agattgcagt cggagcagcc aaagggttgg agtatctgca ccatggctgt | 2400 |
| gagaggctag tgattcatag agatgtcaag tcgagtaaca ttttgttaga tgagttttg | 2460 |
| aagcccccgga tcgcggattt tgggctcgcc aagatggttc agactaatgc aattaaggac | 2520 |
| tcgtctcatg ttgttgctgg aacacacggt tacatagctc ctgaatatgg ttacacctac | 2580 |
| aaggtgaatg agaagagcga tgtgtatagc tttggtgtag tactaatgga gctagtgacc | 2640 |
| gggaaaaagc cgatagatcc atcctttggg gacaacaagg acatagtgaa ctggatatgt | 2700 |
| ggcaacctga agagtagaga gagcgtgtta ggtgtggtgg actcgtacgt tcctgaggcc | 2760 |
| tatagggaag aggctatcaa ggtattgaga attgcaattc tatgcacagc taggcttcca | 2820 |
| gagctaagac cttccatgag aagtgtcgtt caaatgcttg aagaagctca cgagccaatg | 2880 |
| aaaattgctgg acattgttat cagcaaagat ggttctagta agaaaatgga agtacttaaa | 2940 |
| ggaacagaga agtga | 2955 |

<210> SEQ ID NO 11
<211> LENGTH: 103
<212> TYPE: DNA
<213> ORGANISM: Rosa

<400> SEQUENCE: 11

| | |
|---|---:|
| ttcctttcac caagagagga ttatgtggaa gccattccaa ccatacaagc aacttttaaa | 60 |
| cacctcagaa tgctgaattt cagtggattt ggaattaaga ggc | 103 |

<210> SEQ ID NO 12
<211> LENGTH: 101
<212> TYPE: DNA
<213> ORGANISM: Rosa

<400> SEQUENCE: 12

| | |
|---|---:|
| gattctcatc tgcatcaggt gggacgacta ttatccgctg ctcctgatga tgttgcctat | 60 |
| gttggaatct ggggaatggg gggcttgggt aaaacaacca t | 101 |

<210> SEQ ID NO 13
<211> LENGTH: 107
<212> TYPE: DNA
<213> ORGANISM: Rosa

<400> SEQUENCE: 13

| | |
|---|---:|
| attcccaaag aattatgaga ttaataagga aaagttgatc catcaatagc tcgcacatgg | 60 |
| cttaattcct catagtagaa actcttcagt taggccggag gacattg | 107 |

<210> SEQ ID NO 14
<211> LENGTH: 60
<212> TYPE: DNA
<213> ORGANISM: Rosa

<400> SEQUENCE: 14

| | |
|---|---:|
| gtcagcttgt taccgtacaa agacagattc acaagcttgt ttaattcgcc gaactcttcc | 60 |